US00PP21778P2

(12) United States Plant Patent
Kraan

(10) Patent No.: US PP21,778 P2
(45) Date of Patent: Mar. 15, 2011

(54) ***HYDRANGEA* PLANT NAMED 'BOKRATHIRTEEN'**

(50) Latin Name: *Hydrangea paniculata*
Varietal Denomination: Bokrathirteen

(75) Inventor: Kees Jan Kraan, Papenveer (NL)

(73) Assignee: Boot & Co. Boomkwekerijen BV., Boskoop (NL)

( * ) Notice: Subject to any disclaimer, the term of this patent is extended or adjusted under 35 U.S.C. 154(b) by 0 days.

(21) Appl. No.: 12/592,631

(22) Filed: Nov. 30, 2009

(51) Int. Cl.
*A01H 5/00* (2006.01)

(52) U.S. Cl. ..... Plt./250
(58) Field of Classification Search ..... Plt./250

See application file for complete search history.

*Primary Examiner*—Susan B McCormick Ewoldt
(74) *Attorney, Agent, or Firm*—Penny J. Aguirre

(57) ABSTRACT

A new cultivar of *Hydrangea paniculata* named 'Bokrathirteen' that is characterized by its compact plant habit and its inflorescences that are broadly conical in shape and comprised primarily of sterile flowers that open creamy white in color and change to a light pink color.

2 Drawing Sheets

Genus/species: *Hydrangea paniculata.*
Varietal denomination: 'Bokrathirteen'.

BACKGROUND OF THE INVENTION

The present invention relates to a new and distinct cultivar of *Hydrangea paniculata* and will be referred to hereafter by its cultivar name, 'Bokrathirteen'. 'Bokrathirteen' represents a new panicle *hydrangea*, a deciduous shrub grown for landscape use.

'Bokrathirteen' arose as part of an ongoing breeding program conducted by the Inventor in Booskoop, The Netherlands with the goal of developing new cultivars of *Hydrangea* with compact plant habits and attractive and abundant flowers. 'Bokrathirteen' derived from open pollination of an unnamed proprietary seedling of *Hydrangea paniculata* in summer of 2003. The new cultivar was selected from the resulting seedling as a single unique plant in summer of 2006.

Asexual reproduction of the new cultivar was first accomplished by softwood stem cuttings by the Inventor in Boskoop, The Netherlands in summer of 2006. The characteristics of this cultivar have been determined to be stable and are reproduced true to type in five successive generations.

SUMMARY OF THE INVENTION

The following traits have been repeatedly observed and represent the characteristics of the new cultivar. These attributes in combination distinguish 'Bokrathirteen' as a unique cultivar of *Hydrangea paniculata.*

1. 'Bokrathirteen' exhibits a compact plant habit.
2. 'Bokrathirteen' exhibits inflorescences comprised primarily of sterile flowers.
3. 'Bokrathirteen' exhibits panicles that are broadly conical in shape.
4. 'Bokrathirteen' exhibits flowers that open creamy white in color and quickly change to a light pink color.

The new cultivar of *Hydrangea* differs from its female parent plant, an unnamed seedling, in having a greater number of sterile flowers that emerge creamy white in color and turn light pink, whereas the female parent exhibits a large proportion of fertile flowers and has sterile flowers that emerge creamy white and change to a dark pink color. 'Bokrathirteen' can be most closely compared to the cultivars 'Limelight' (U.S. Plant Pat. No. 12,874) and 'Bombshell' (U.S. Plant Pat. No. 21,008). 'Limelight' differs from 'Bokrathirteen' in having sterile flowers that are greenish white in color and in having panicles that are more conical in shape. 'Bombshell' differs from 'Bokrathirteen' in having sterile flowers that are white with a red eye and turn darker pink as they mature and in having panicles that are more rounded in shape.

BRIEF DESCRIPTION OF THE DRAWINGS

The accompanying photographs were taken in September of a two year-old plant of 'Bokrathirteen' as field grown in Boskoop, The Netherlands.

The photograph in FIG. 1 illustrates the plant habit and flowers of 'Bokrathirteen' in bloom.

Figure 1:
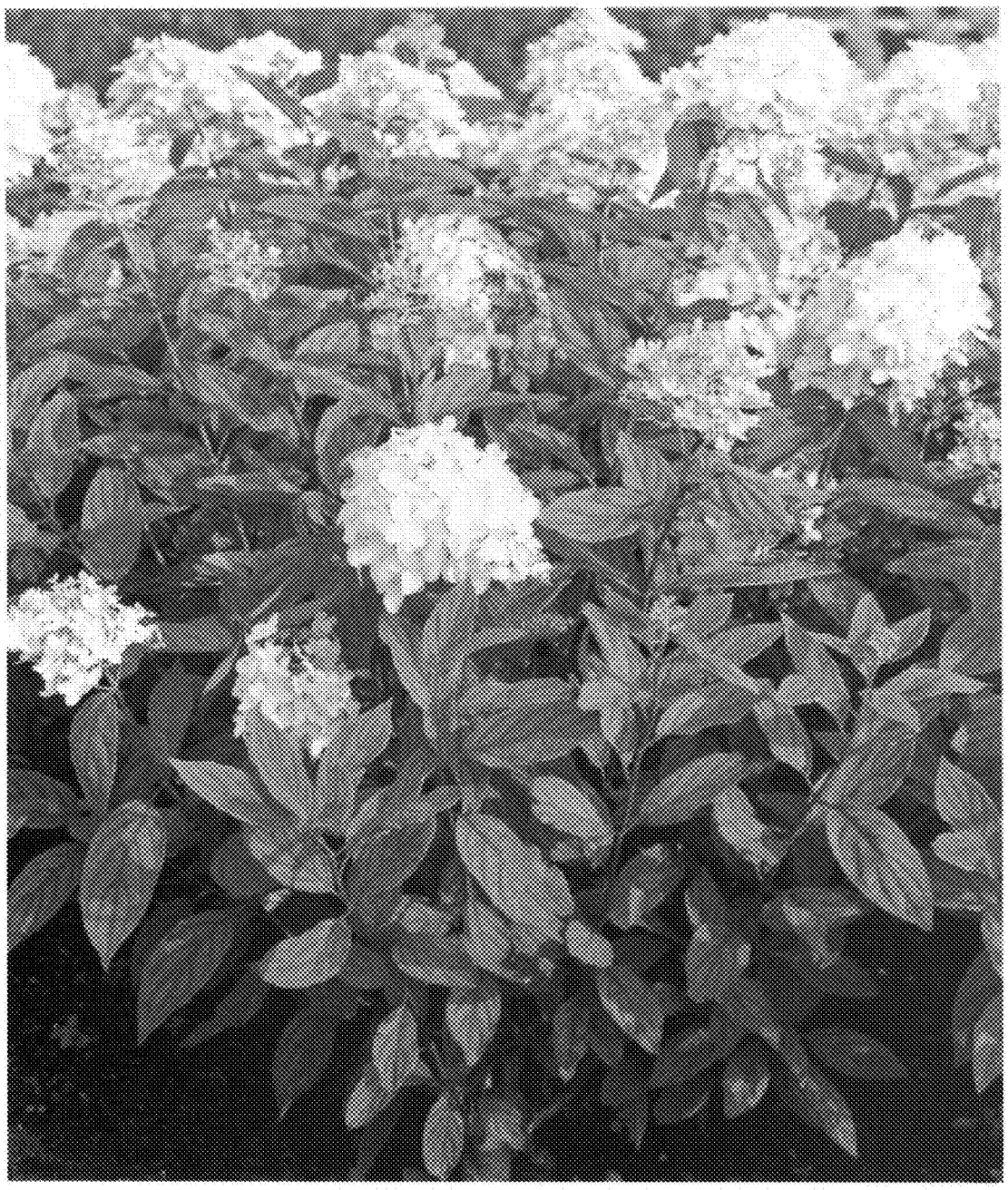
Figure 2:
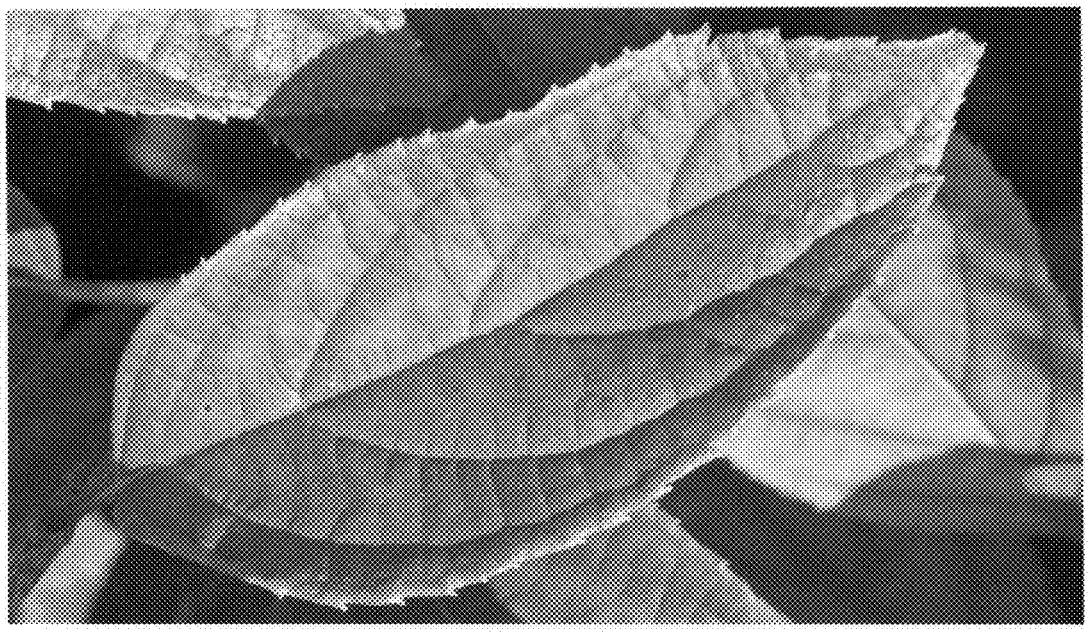

The photograph in FIG. 2 provides a close-up view of a leaf of 'Bokrathirteen'.

Figure 3:
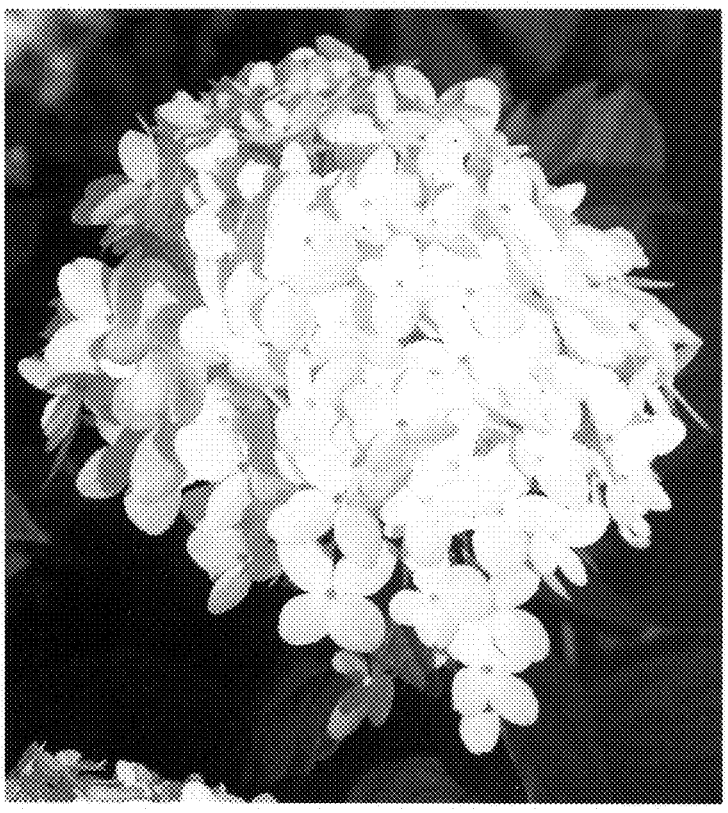

The photograph in FIG. 3 provides a close-up view of an inflorescence of 'Bokrathirteen' that is just starting to turn in color.

The colors in the photographs may differ slightly from the color values cited in the detailed botanical description, which accurately describe the colors of the new *Hydrangea.*

BOTANICAL DESCRIPTION OF THE PLANT

The following is a detailed description of two year-old plants of the new cultivar as field grown in Boskoop, The Netherlands. The plants were grown under average day temperatures of 14° C. to 30° C. and average night temperatures of 4° C. to 16° C. Phenotypic differences may be observed with variations in environmental, climatic, and cultural conditions. The color determination is in accordance with The 2007 R.H.S. Colour Chart of The Royal Horticultural Society, London, England, except where general color terms of ordinary dictionary significance are used.

General description:

*Blooming period.*—Mid to late summer in Boskoop, The Netherlands.

*Plant habit.*—Broadly upright, globular in overall shape, compact.

*Height and spread.*—Reaches about 73 cm in height and 57.5 width at 2 years in age.

*Hardiness.*—At least in U.S.D.A. Zones 4 to 9.

*Diseases.*—No susceptibility or disease resistance has been observed.

*Environmental tolerance.*—Panicles exhibit good tolerance to wind and rain.

*Root description.*—Slightly fibrous and moderately dense.

*Growth rate.*—Moderate.

Growth and propagation:

*Propagation.*—Softwood stem cuttings.

*Root initiation.*—About 30 days under greenhouse conditions with soil temperatures of 20° C.

*Finishing time.*—Average of 26 weeks from propagation to produce a fully rooted plant with an average air temperature of 18° C.

Stem description:

*Stem shape.*—Round, solid.

*Stem strength.*—Strong.

*Stem aspect.*—Upright to 45°.

*Stem color.*—New growth; 184A to 184B, mature; to 199A to 199B.

*Stem size.*—Average of 38.3 cm in length, average of 5 mm in width.

*Stem surface.*—Glabrous and smooth, mature stems are moderately covered with lenticels; 7 per square cm, an average of 2 mm in length, 1 mm in width, N199D in color.

*Internode length.*—Average of 4.9 cm.

*Branching.*—Freely branched, a two year-old plant will produce an average of 7 lateral branches, pinching improves branching.

Foliage description:

*Leaf shape.*—Ovate.

*Leaf arrangement.*—Opposite, occasionally in whorls of 3.

*Leaf division.*—Simple.

*Leaf base.*—Broadly cuneate to rounded.

*Leaf apex.*—Short acute to short apiculate.

*Leaf margins.*—Serrate.

*Leaf venation.*—Pinninerved, recessed on upper surface, color 147C on upper surface and 148C on lower surface.

*Leaf size.*—Average of 9.7 cm in length and 4.5 cm in width.

*Leaf attachment.*—Petiolate.

*Leaf surface.*—Upper and lower surfaces; dull, very slightly rugose, pubescent and very sparsely covered with short adpressed hairs averaging 0.8 mm in length and 157C and 157D in color.

*Leaf color.*—Young leaves upper surface; range from 144A to 146A , young leaves lower surface; 147C, mature leaves upper surface; N137C to 137D, mature leaves lower surface; 138B.

*Petioles.*—Average of 1.4 cm in length and 2.5 mm in width, dull in texture, sparsely pubescent with very short hairs 0.4 to 0.7 mm in length and 157C to 157D in color, upper surface 152B in color with edges 175A, lower surface 146C to 146D in color.

Inflorescence description:

*Inflorescence type.*—Terminal panicles, broadly conical in shape, comprised of rotate, star-shaped sterile flowers above very few fertile flowers.

*Lastingness of inflorescence.*—Sterile flowers persistent, but summer color is retained for about 4 weeks, fertile flowers short lived and self-cleaning.

*Inflorescence number.*—One per lateral or sublateral stem if pinched.

*Inflorescence size.*—Average of 13.4 cm in height and 13.8 cm in diameter.

*Flower number.*—Numerous, average of about 350 sterile flowers and about 80 fertile flowers per inflorescence.

*Flower fragrance.*—None.

*Flower aspect.*—Upright to outward (sterile flowers).

*Flower size.*—Sterile flowers; an average of 3.8 cm in diameter and 1 cm in depth, fertile flowers; an average of 1.2 cm in diameter and 9 mm in depth.

*Flower buds.*—Sterile flowers; an average of 5 mm in length and 4 mm in diameter, broadly obovate in shape, 145C to 145D in color, Fertile flowers; an average of 3 mm in length and 2 mm in diameter, broadly ovate in shape, 157C to 157D in color with apex flushed with 63C.

*Peduncles.*—Strong, extension of stem, average of 7 cm in length and 2.5 mm in width, 199A to 199B in color, surface is glabrous and smooth.

*Pedicels.*—Sterile flowers; moderate strength, an average of 1.7 mm in length and 1 mm in width, NN155A in color, surface is smooth and dull, held between 70° and 110° angle (average 85°), fertile flowers; an average of 1.5 mm in length and 0.5 mm in length, 157D in color, moderate in strength, texture is smooth and dull, held in all directions.

*Fertile flowers.*—Petals; 5, rotate, an average of 4 mm in length and 2 mm in width, ovate in shape, acute apex, cuneate base, entire margin, color upper surface opening and mature; NN155C to NN155D, color lower surface opening; NN155A with apex 62C, color lower surface mature; NN155C to NN155D, upper and lower surface smooth and glossy, sepals; 5, rotate, an average of 1 mm in length and 0.8 mm in width, ovate to triangular in shape, acute apex, broadly cuneate base, entire margin, color upper and lower surface opening; 157A to 157B, color upper and lower surface mature; 157B to 157C.

*Sterile flowers.*—Sepals; an average of 4, un-fused, rotate in arrangement, smooth, dull and glabrous on both surfaces, broadly elliptic to obovate in shape, entire margin, apex is rounded to obtuse, cuneate base, an average of 1.9 cm in length and 1.4 cm in width, color upper and lower surface when newly opened, upper and lower surface; 155A to 155B, color when mature, upper surface; ranges from 184B to 185C, color when mature, lower surface; 145C flushed with 182C and 182D (particularly towards margins), center (eye of sterile flowers, reduced petals); 1.5 mm in diameter, 2 mm in length, broadly ovate in shape, 155A to 155B in color with apex 63C.

Reproductive organs (fertile flowers):

*Stamens*.—Average of 8, anther is double kidney-shaped, about 1 mm in length and 155A to 155B in color, filament is an average of 5.5 mm in length and 155C to 155D in color, pollen was low in quantity and 156B to 156C in color.

*Pistils*.—Average of 3, average of 1.2 mm in length, style is an average of 1 mm in length and 155C in color, stigma is flattened on top of the style and 155C to 155D in color, ovary is 145C to 145D in color.

*Fruit and seed*.—None observed.

It is claimed:

1. A new and distinct cultivar of *Hydrangea* plant named 'Bokrathirteen' substantially as herein illustrated and described.

* * * * *